United States Patent
Savage, Jr. et al.

(10) Patent No.: US 6,811,563 B2
(45) Date of Patent: Nov. 2, 2004

(54) PORTABLE LIGHT DELIVERY APPARATUS AND METHODS FOR DELIVERING LIGHT TO THE HUMAN BODY

(75) Inventors: Henry C. Savage, Jr., 352 W. 1060 South, Orem, UT (US) 84058; Kent W. Savage, American Fork, UT (US); Steven D. Powell, Orem, UT (US)

(73) Assignee: Henry C. Savage, Jr., Orem, UT (US)

( * ) Notice: Subject to any disclaimer, the term of this patent is extended or adjusted under 35 U.S.C. 154(b) by 0 days.

(21) Appl. No.: 10/339,968

(22) Filed: Jan. 9, 2003

(65) Prior Publication Data
US 2004/0138726 A1 Jul. 15, 2004

(51) Int. Cl.[7] .............................................. A61N 5/06
(52) U.S. Cl. ............................ 607/88; 606/9; 607/89
(58) Field of Search ............................ 606/9; 607/88–94

(56) References Cited

U.S. PATENT DOCUMENTS

| | | | | |
|---|---|---|---|---|
| 6,045,575 A | * | 4/2000 | Rosen et al. .................. | 607/88 |
| 6,046,401 A | * | 4/2000 | McCabe ..................... | 136/244 |
| 6,290,713 B1 | * | 9/2001 | Russell ........................ | 607/88 |
| 6,443,978 B1 | * | 9/2002 | Zharov ........................ | 607/89 |
| 6,454,791 B1 | * | 9/2002 | Prescott ....................... | 607/89 |
| 6,471,716 B1 | * | 10/2002 | Pecukonis .................... | 607/89 |
| 6,596,016 B1 | * | 7/2003 | Vreman et al. ............... | 607/88 |
| 6,669,627 B1 | * | 12/2003 | Campbell et al. ............. | 600/27 |
| 2003/0187486 A1 | * | 10/2003 | Savage et al. ................ | 607/89 |
| 2003/0233138 A1 | * | 12/2003 | Spooner ....................... | 607/93 |

* cited by examiner

Primary Examiner—Roy D. Gibson
Assistant Examiner—Henry M Johnson, III
(74) Attorney, Agent, or Firm—Kulaniakea Fisher; Rader, Fishman & Grauer

(57) ABSTRACT

A device is provided for delivering light to the blood supply of a human body through a non-ocular skin area. The device has a plurality of light emitting diodes (LEDs) spaced apart from each other and extending through apertures for emitting light to the body and a power supply connected to the light delivery unit. The device provides wavelengths of light within a specifically-determined range of intensity and a specifically-determined angles of illumination. Devices may be included for controlling and programming the output of the LEDs. A method is provided for delivering light to a non-ocular body region for treating jaundice, breaking down bilirubin and treating other disorders.

46 Claims, 7 Drawing Sheets

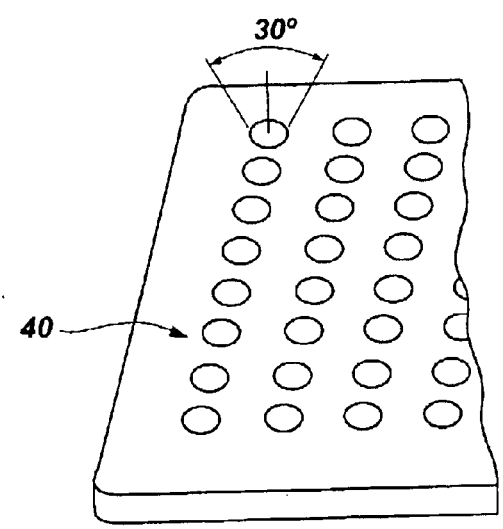 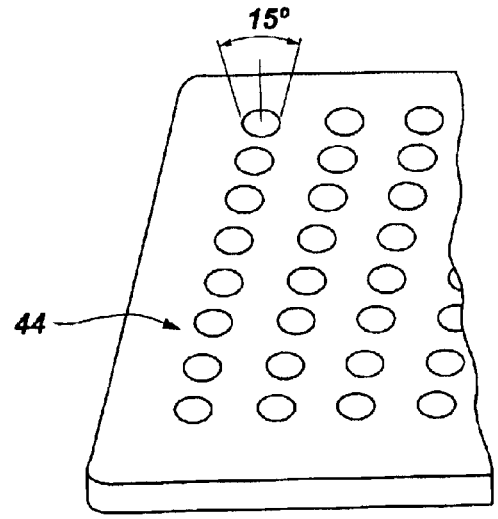
Fig. 4A  Fig. 4B
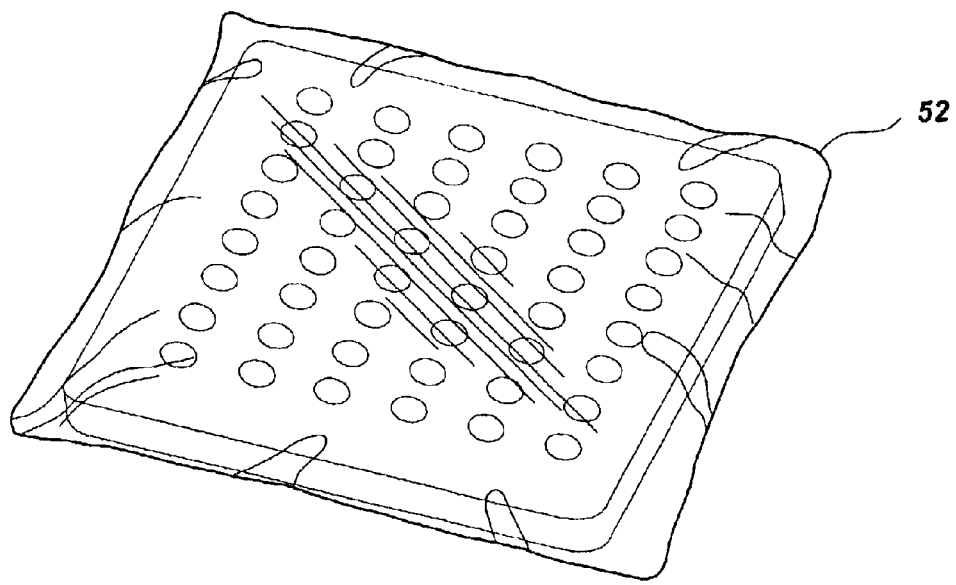
Fig. 5

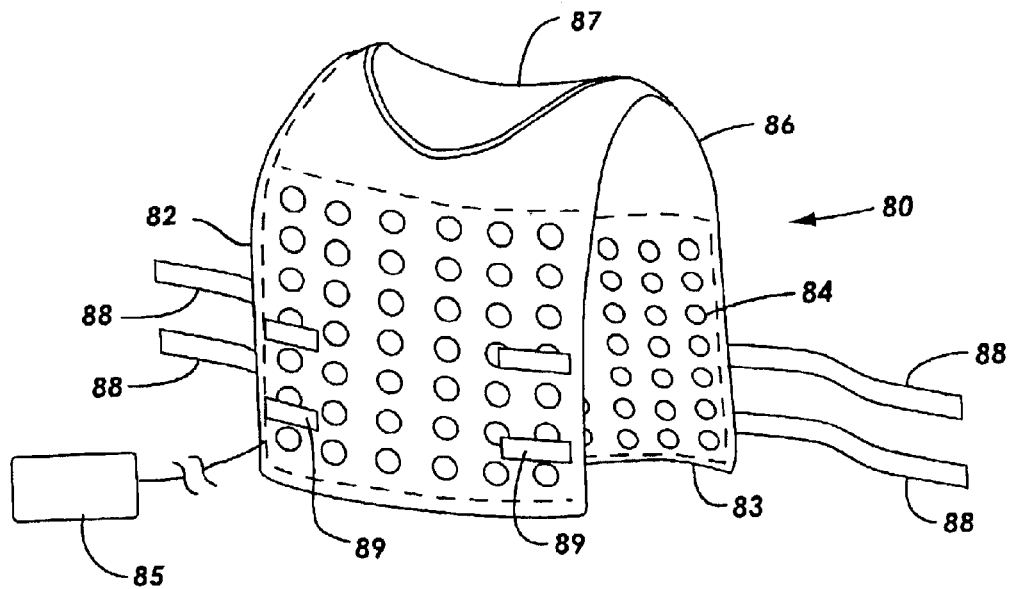
FIG. 8A
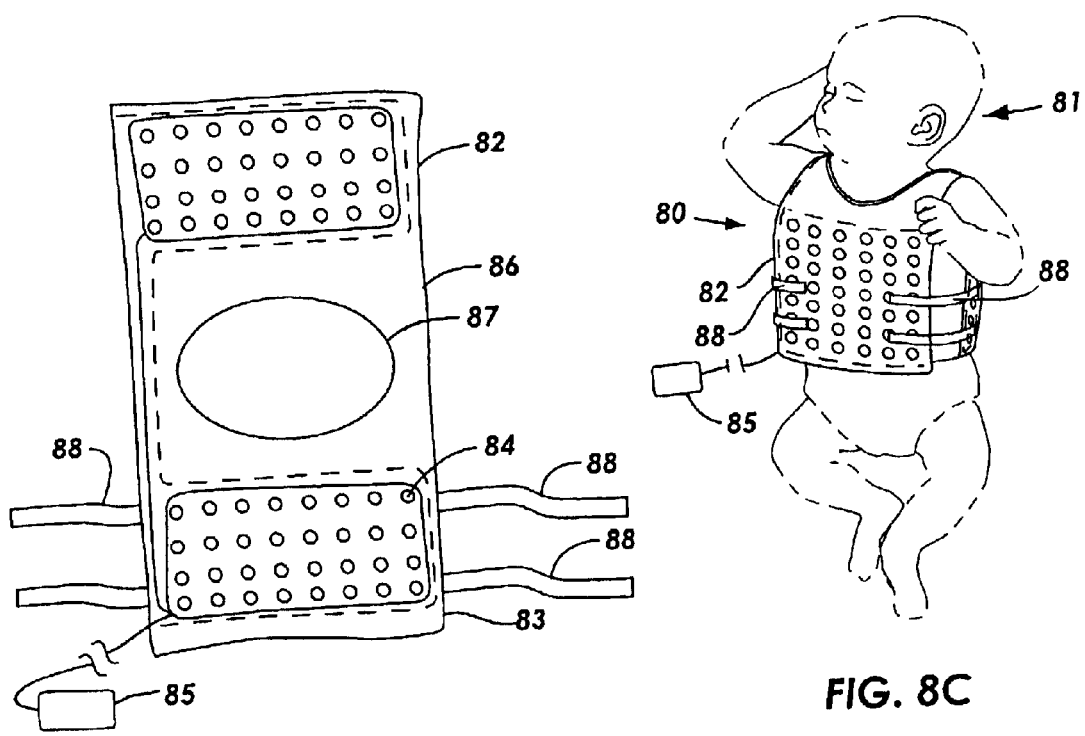
FIG. 8B
FIG. 8C

PORTABLE LIGHT DELIVERY APPARATUS AND METHODS FOR DELIVERING LIGHT TO THE HUMAN BODY

GOVERNMENT RIGHTS

The portable light delivery apparatus and methods for delivering light to the human body was developed with Government support under Grant No. 1R1MH61043-01, awarded by the National Institute of Health. The Government may have certain rights in this application.

BACKGROUND

1. Field of the Invention

This disclosure relates to a portable device for delivering light to the blood supply of a human body to treat jaundice, excessive bilirubin, mood disorders, sleep and body cycle problems in humans. More particularly, the present disclosure concerns a portable planar light delivery pad, and methods related thereto, for delivering light to the blood supply by exposing a non-ocular portion of the body to light at pre-selected wavelengths and intensity, particularly for the treatment of excessive bilirubin in infants and others.

2. The Related Art

Bilirubin is the waste product that results from the breakdown of hemoglobin molecules from worn out red blood cells. Ordinarily, it is excreted from the body as the chief component of bile. Excessive levels of bilirubin stain the tissues in the skin yellow, resulting in what is called jaundice. Very high levels of bilirubin in the bloodstream can cause permanent damage to certain areas of the brain of newborn infants, referred to as kernicterus. This can cause a characteristic form of crippling known as athetoid cerebral palsy. To prevent this from happening, bilirubin levels are closely monitored in newborns. Excessive levels of bilirubin are treated by either phototherapy ("bilirubin lights") or exchange transfusion.

Regarding phototherapy, other problems and disorders have been found to respond to the application of light to non-ocular areas of the body. These include seasonal affective disorder, mood disorders and sleep-related disorders, such as the disorientation of the human circadian cycle that often results from traveling through various time zones, commonly referred to as "jet lag."

In light therapy, it has also been determined that some wavelengths of light are more effective in treating certain disorders than others. Thus, treatment using light with a single wavelength or a plurality of wavelengths within a fairly narrow range is often used. Blue light has been found to most effective in breaking down bilirubin, referred to as neonatal phototherapy. In addition, it may be desirable, wherever possible to treat the infant or other patient as an out-patient, rather than admitting them to the hospital.

Phototherapy has traditionally been conducted using fluorescent blue light therapies or blue fiberoptic therapies. One problem with fluorescent blue light therapy is that it may provide additional light in a broader bandwidth than necessary. In addition, fluorescent light banks or boxes emit a substantial amount of heat causing substantial discomfort and possibly even danger to newborn infants. Light banks or boxes are not portable, requiring the baby to remain in one location. The mother or other attendants are not able to care for it during fluorescent phototherapy. In addition, the light is directed to the entire body, including the eyes, requiring eye shields or shades to be used. Consequently, light banks or boxes are not as conducive to use by outpatients at home.

Fiberoptic therapy is slightly more conducive for outpatient use, since the light generator and fiber-optic system are small enough to bring to a patient's home. One difficulty with blue fiberoptic therapy is that the light generation source and light delivery system may be complicated and expensive. Fiberoptic lamp units also produce excessive heat that can be troublesome. The lamp required for generating light for a delivery system has a relatively short life (200–300 hours), is expensive and therefore complicates the delivery of light to an outpatient.

U.S. Pat. No. 6,135,117 (Campbell et al.) discloses a method for providing non-ocular light to the body using a large fiber-optic light pad to treat jaundice in newborns. The system is described as being useful for treating circadian rhythm problems and various sleep disorders. The pad is attached to a bulky high-intensity light supply and requires a large delivery line running from the light supply to the pad. Campbell also indicates that the delivery of extra-ocular light stimulus to the body can mediate and shift the phase of a circadian cycle. However, the Campbell system is encumbered by the above-mentioned disadvantages with respect to fiber-optic systems.

Regarding exchange transfusion, this approach is an expensive, difficult and somewhat dangerous process, since blood from external sources is being introduced to the body. The process is also invasive and cumbersome, requiring the patient to remain at the same location and substantially immobile during the exchange process. Consequently, it is of very limited usefulness, although it can be invaluable in a crisis.

Some systems have been developed to deliver light to the vascular tissues using light emitting diodes (LEDs). U.S. Pat. No. 6,290,713 (Russell) discloses an apparatus for providing light from LEDs to infants and others to treat light-related illnesses. A flexible substrate has LEDs mounted on the substrate to direct light to the patient. However, a cover is placed over the LEDs with light diffusers thereon, such as glass bubbles or reflectors. The diffusers are meant to distribute light more evenly. However, they cause a substantial attenuation in the amount of light directed to the patient, so that more power must be applied to the LEDs to attain the amount of light needed. As a result, extensive cooling systems are required for the Russell device to conduct away excessive heat. These problems make the Russell device relatively complicated and expensive to produce and use.

More recent research has been directed to the possible use of LEDs as light delivery elements for providing light therapy. A recent article by Vreman, Wong and Stevenson broadly discussed the possible future use of surface mount LEDs mounted on rigid or flexible low voltage circuit boards to form devices such as canopies, pads, blankets and even clothing. See Vreman et al, "Light Emitting Diodes For Phototherapy For the Control of Jaundice," Biologic Effects of Light 2001, p. 355, Kluwer Academic Publishers (Symposium June 2001). However, the Vreman article described the use of surface mounted LEDs, which would be likely to encounter difficulties similar to those of the Russell device.

Accordingly, there exists a need for a light delivery system that provides light to a patient simply and effectively, with a minimum of heat and complicated apparatus. A further need exists to be able to apply monochromatic light to eliminate unnecessary light and heat. Yet another need exists to provide a light delivery system that is light-weight, flexible and uniform in the application of light to the body.

Another possible need exists for a light delivery device to allow handling and treatment of the patient by caregivers during therapy. Additionally, a light-delivery source is needed that has long life and requires little maintenance. A yet further need exists for a light delivery system that can control the amount of power directed to the light source, to minimize the amount of heat to which the patient is exposed, and to time the exposures according to the specific needs of each patient. Another need exists to have a light-therapy system that is able to treat a variety of problems, including jaundice, excess bilirubin, seasonal affective disorders, sleep-related disorders and mood disorders.

SUMMARY

The present disclosure involves providing light to areas of the body where there are substantial blood vessels near the surface of the skin, the vascular tissue regions, so that the light can interact with photoactive substances in the blood to correct various problems. Several effective areas for the administration of light have been found, such as the popliteal region, the area directly behind the knee joint, as well as the chest, neck, arm and abdominal area. In treating jaundice for newborn infants, the abdominal area has been found to be most advantageous because of ease in access, extensive vascular tissue close to the skin and because the delivery unit can be blanket shaped to be comfortable and cover a relatively large area. The use of LEDs makes the device light-weight, inexpensive, low in heat output and able to deliver different wavelengths of light as needed. LEDs also provide a light delivery source that has a long life of several years and requires little or no maintenance.

The structure of the portable light delivery apparatus enables the LEDs to be mounted in a through-hole arrangement to provide maximum bright exposure with a minimum amount of heat. A controller enables the intensity of the light to be varied, and switching apparatus enables the light to be administered in duty cycles, maximizing the light penetration while maintaining the heat at tolerable levels. Some or all of the controller circuitry may be remote from the patient, lessening exposure to heat. A programmable device may be included as part of the controller for timing and sequencing the application of light, thereby customizing the photo-therapy to accommodate each patient's needs.

In one implementation of the portable light delivery apparatus, a portable light-emitting device is provided for delivering light to the blood supply of a human body of a subject through a non-ocular area of skin on the body. A light delivery unit having multiple spaced-apart apertures therein is disposed for positioning on a portion of the body. A plurality of individual light sources are each disposed within one of the apertures of the light delivery unit for directing light toward the body. A power supply is connected to the light delivery unit for delivering power to the light sources. A controller unit is disposed between the power supply and the light delivery unit for controlling the delivery of power to the light sources.

In another implementation, a light-emitting device is provided for delivering light to the blood supply of a human body of a subject through a non-ocular area of skin on the body. A flexible unit is provided for positioning on a portion of the body having a plurality of spaced apart apertures therein. A plurality of light emitting diodes (LEDs) are each disposed on the flexible unit to extend through one of the apertures to direct light to the body. A power supply is connected to the LEDs for delivering power thereto.

In a further implementation, a method is provided using a portable light-emitting device to deliver light to the blood supply of a human body of a subject through a non-ocular area of skin on the body. A light delivery unit having multiple spaced-apart apertures therein is positioned on a portion of the body. Light is directed to a portion of the body from a plurality of individual light sources, each being disposed within one of the apertures of the light delivery unit. Power is provided to the light sources from a power supply connected to the light delivery unit. The delivery of power to the light sources is controlled with a controller unit disposed between the power supply and the light delivery unit.

In yet another implementation, a method is provided of using a light-emitting device to deliver light to the blood supply of a human body of a subject through a non-ocular area of skin on the body. A flexible unit having a plurality of spaced apart apertures therein is positioned on a portion of the body. A plurality of light emitting diodes (LEDs) are disposed on the flexible unit, each LED extending through one of the apertures to direct light to the body. Power is provided to the LEDs from a power supply connected to the LEDs for delivering power thereto.

The foregoing apparatus and methods may be used to effectively treat an infant for jaundice, to treat any subject for an excess of bilirubin or to provide photo-therapy for a number of illnesses and disorders, including seasonal affective disorders, sleep-related disorders and mood disorders.

BRIEF DESCRIPTION OF THE DRAWINGS

FIGS. 4A and 4B are schematic views showing different angles of illumination for LED arrays of the portable light delivery apparatus;

FIG. 5 is a schematic view showing an implementation having waterproof sealing around the LED array;

FIGS. 8A–8C are schematic views showing an alternative vest implementation; and

DETAILED DESCRIPTION

The present provides a light delivery apparatus that may be portable, wearable, lightweight and easily supplied with power. The LEDs provide a simple and relatively inexpensive source of light. The LEDs have much longer life than prior light sources, such as fiber-optic lamps, and require less maintenance.

The LEDs may be through-hole devices that are mounted in apertures extending through a pad, so that light can be directed to the subject with a minimum of interference. The LEDs have the capability of delivering light energy at wavelengths within a pre-selected wavelength range and at or above a pre-selected light intensity. The pad may be connected to a stationary power source or to batteries. In either case, the pad may be wrapped around a portion of the body so that it can be worn while the subject moves about.

In treating infants for jaundice or other problems, light should be delivered to the body as long as possible to quickly reduce the bilirubin level in the infant's body. With the present disclosure, the pad may be wrapped around the infant like a blanket so that the caregiver can hold the child, feed it or attend to other needs while the light is being delivered to the body. The pad is flexible because of thin substrate strips connected together to form a flexible light treatment pad or blanket.

The Apparatus

Figure 1A:
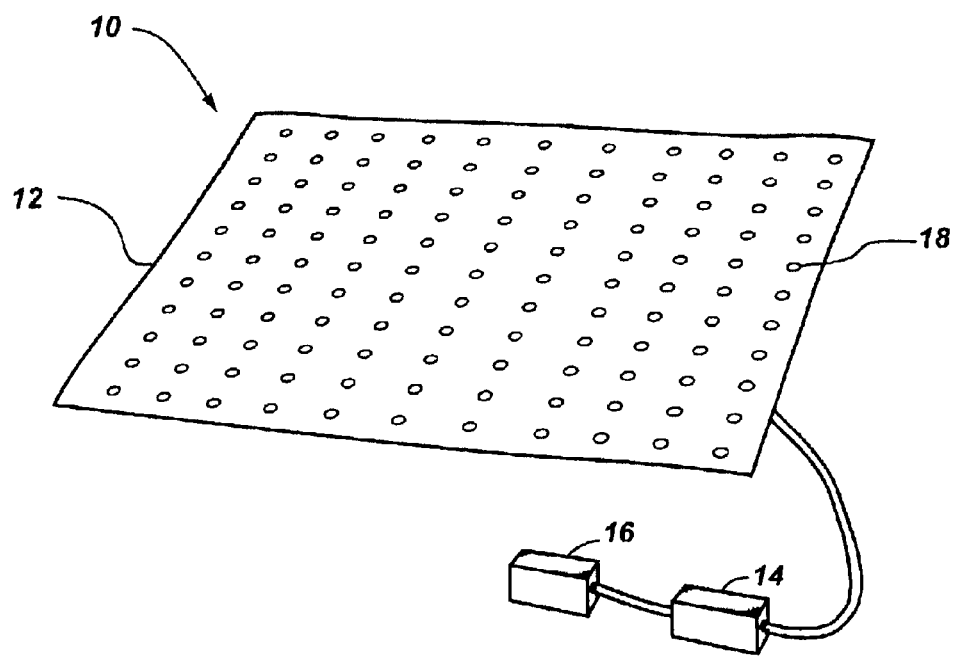
FIGS. 1A and 1B are perspective, schematic views of one implementation of the portable light delivery apparatus.
Figure 1B:
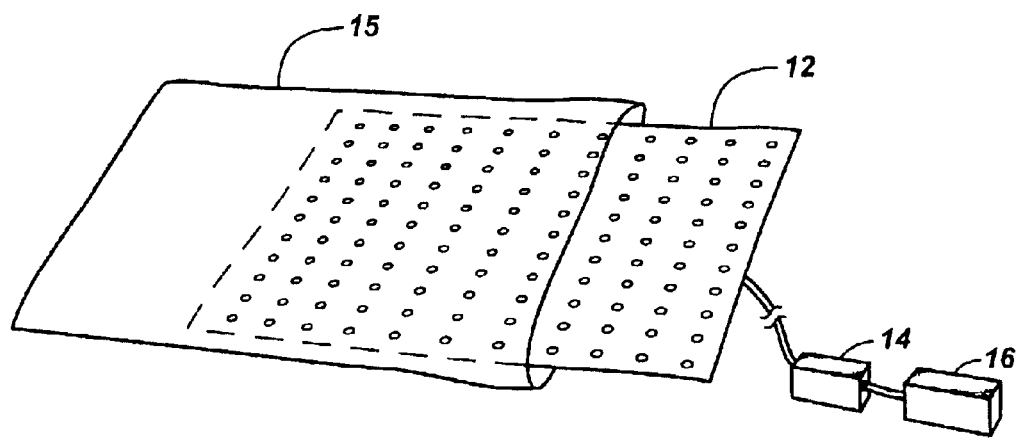

Referring now to FIGS. 1A and 1B, one implementation of the light treatment pad of the present disclosure is shown generally at 10. The apparatus includes a light pad 12, a controller 14 and a power source 16. Preferably pad 12 has a plurality of apertures 18 that may be arranged in rows and columns on the pad. A plurality of through-hole LEDs (not shown) are each disposed in one of apertures 18 to direct light from the pad toward a subject's body. The power source 16 may be either an AC/DC transformer to plug into a power socket or a small battery pack, not shown, to enable the entire unit to be portable.

Figure 2A:
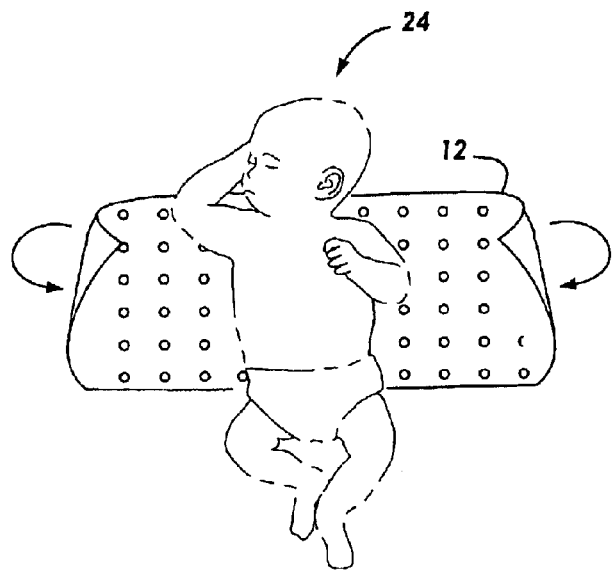
FIGS. 2A–2D are illustrations regarding the use of the apparatus shown in FIG. 1, and a variation thereof, for treating an infant for jaundice.
Figure 2B:
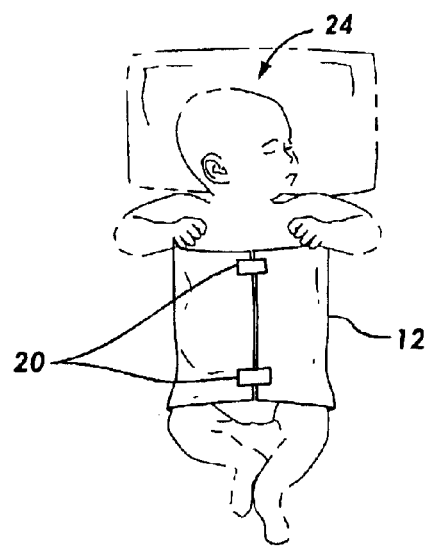
Figure 2C:
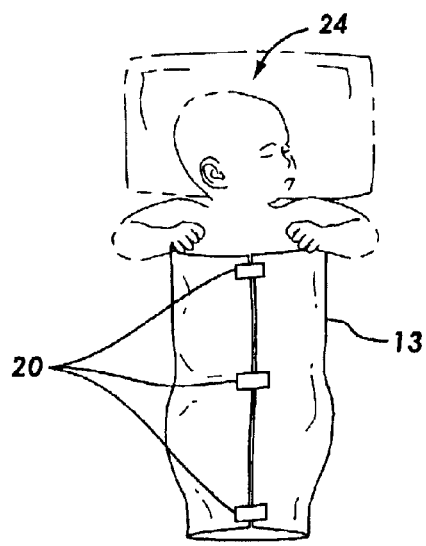

The pad 12 is made of a lightweight cushioned material, such as a foam material and may be generally rectangular in shape. In one implementation, the pad 12 is of a size, such as five inches by nine inches, so as to either lay the upper torso of an infant 24 on it, as shown in FIG. 2A or to comfortably wrap the pad completely around the upper torso of infant 24, as shown in FIG. 2B. Alternately, as shown in FIG. 2C, a larger pad 13 may be shaped to fit around the entire lower body of the infant 24. In either case, fasteners 20, such as hook and loon fastener strips, can be applied to secure the pad 12 or 13 around the infant 24.

Figure 2D:
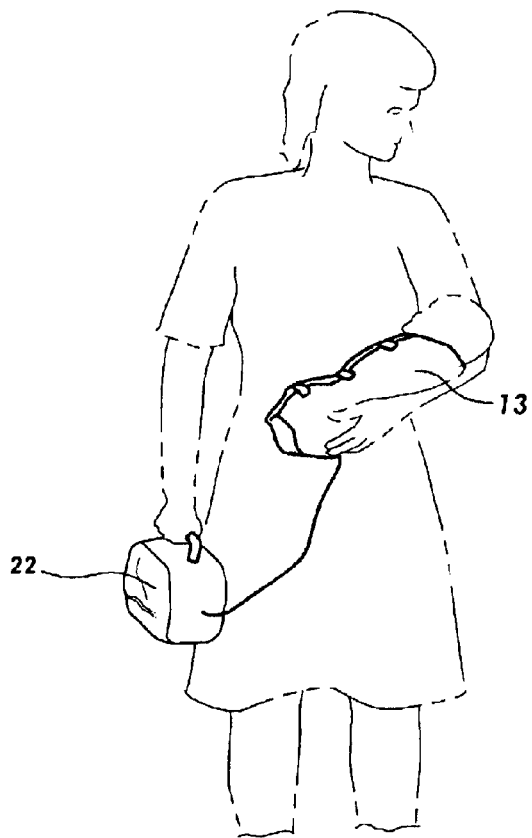

As shown in FIG. 2D, a portable container, such as case 22, can be used to contain the controller 14 and the battery pack 16 so that a mother or other caretaker can take the infant on any desired errand while the light treatment is continued.

One implementation utilizes an array of nine by sixteen LEDs, each powered at about five milliamps of current, with each LED having a voltage of about 3.3 volts. In such case, the array may operate effectively at about 9.9 volts with 240 milliamps. If the power source 16 is a transformer, the supply voltage can be rated at nine volts and 400 milliamps. If the power source 16 is a battery pack, it may comprise a nine-volt rechargeable Ni-MH or NiCad battery, or a twelve-volt sealed lead acid battery pack.

Controller 14, is used to provide voltage and current control to the LEDs. The LEDs must have a minimum amount of power to function properly. In the event that controller 14 does not receive the necessary minimum amount of power from the power source 16, it will first indicate that power is diminished, and then as the power is reduced below an acceptable level, the controller 14 will switch off all power to the LEDs. Likewise, in the event of an undesirable power surge, controller 14 cuts off power to the LEDs or reduces power to an acceptable level. Similarly, controller 14 can also be used to shut off power to the LEDs in the event of a short circuit or other malfunction.

As shown in FIGS. 1A–B, it may be preferable to provide sufficient cord length for the power source 16, particularly in its transforming function, as well as the controller 14 to be situated distant enough from the subject to dissipate any heat generated by the functions of the power source and the controller without exposing the infant to any appreciable amount of heat. This design maximizes the comfort of the infant by exposing it to a minimum amount of heat.

In an alternate implementation, controller 14 may be mounted on the battery pack power source 16 to provide a single unit that may be more readily carried by the user. Separating the power source 16 and controller 14 from the light pad 12 may be advantageous, in that only the light pad 12 needs to be positioned on the infant during extended light delivery treatment, particularly during sleep times. Therefore, the bulk on or near the infant is minimized and the comfort of the subject is enhanced.

In addition to the functions described above, the controller 14 may also include a conventional programming device (not shown), as well as input keys, to provide the desired program for the controller to follow. Alternately, the programming device may be separated from the light delivery apparatus to minimize the weight and bulk to be carried by the patient. In such case, the programmer could be a separate device that would only be attached at certain rest periods so as change the programming of the controller, as desired.

Figure 3A:
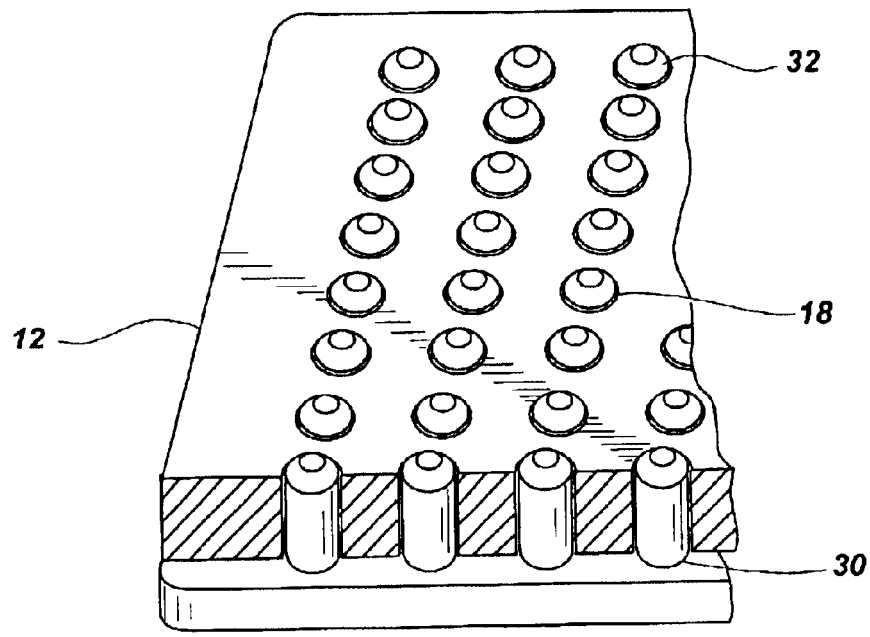
FIGS. 3A and 3B are schematic views showing LEDs mounted relative to the pad of two different implementations.
Figure 3B:
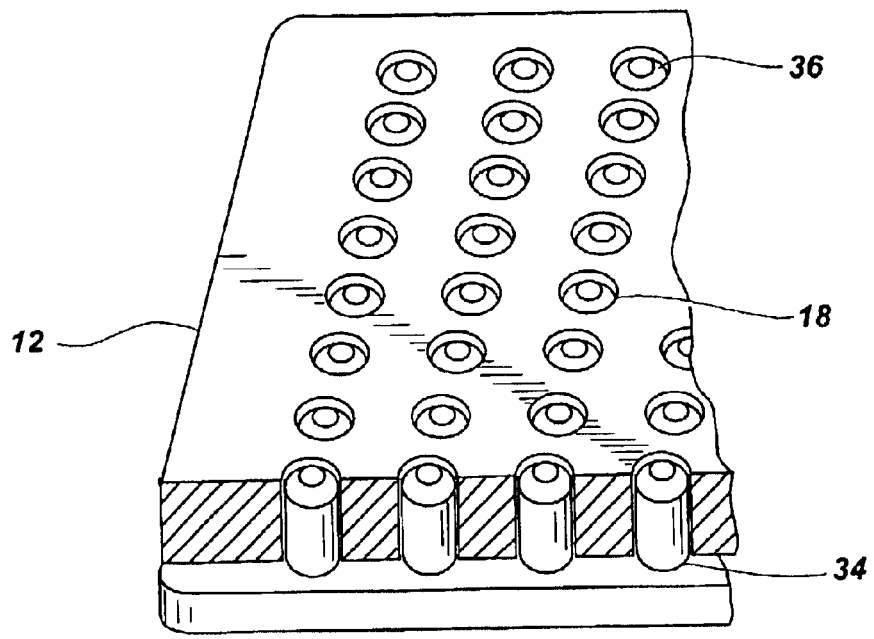

As shown in FIG. 3A, light pad 12 includes a plurality of through-hole LEDs 30 mounted therein. The pad 12 may be punched with tapered holes 18 that fit over rigid LED strips, shown later. The pad 12 is manufactured to keep the LEDs away from the skin, provide a cushioned feel and not block light emitted from the LEDs. Each LED 30 extends into one of the apertures 18 so that the top 32 of each LED 30 may be essentially flush with the upper surface of light pad 12, as shown in FIG. 3A. Alternately, as shown in FIG. 3B, LEDs 34 may be mounted so the tops 36 of each LED 34 are slightly recessed in each aperture 18 relative to the upper surface of light pad 12, as shown in FIG. 3B.

Preferably, the light pad 12 is placed in direct contact with the region of the body to be treated. Since none of the LEDs 30 extends above the upper surface of light pad 12, the LEDs are not in direct contact but in close proximity to the skin of the patient. Thus, no undue pressure points are provided that could cause discomfort or interfere with the circulatory integrity and comfort of the region to be treated.

The use of LEDs enables light to be directed within different angles, ranging from very narrow to a wide pattern. A narrow pattern is more intense and will penetrate deeper into the skin. However, a narrow pattern will not cover as large of a surface area of the skin. The implementations incorporate LEDs having angles that will penetrate deep enough into the skin tissue to be effective, yet wide enough to cover the important surface area of the skin.

FIGS. 4A and 4B show different implementations using LEDs with different angles of illumination. In FIG. 4A, an array of LEDs 40 provides an angle of illumination of about 30°, considered a relatively broad diffusion of light. Using this type of LED array, the light delivery will be more diffuse to cover a greater area, but is not likely to have as much intensity as more focused light delivery. The light delivery system is likely to function better where there are an abundance of blood vessels relatively close to the surface of the skin. In that situation it would be advantageous to deliver light to a broad area with less need for light penetration.

Conversely, in FIG. 4B, an array of LEDs 44 provide an angle of illumination of about 15°. This approach results in greater intensity and less diffusion of the light delivery system. This type of LED is most effective where there are not as many blood vessels near the surface of the skin, and greater light penetration is needed.

The use of LEDs in the present disclosure makes it possible to install LEDs in the apparatus of the present disclosure that all have the same frequency or wavelength.

This enables the application of specific light frequencies or wavelengths that are most effective in treating specific problems. For example, as stated above, blue light has been found to be most effective in breaking down bilirubin in the blood supply. Specifically, light having wavelengths in the range of 460–480 nanometers have been determined to be effective in bilirubin treatment. Other examples of specific light wavelengths that have been found to be effective in the industry in treating various problems include about 660 nm for treating wounds, cuts, scars and infections; 405–420 nm for treating acne; 465–470 nm, particularly 467 nm for treating sleep disorders and circadian cycle problems.

In one example, 30° LEDs 40 shown in FIG. 4A were used having monochromatic light at a wavelength of about 470 nanometers. The forward voltage provided a current of about 20 milliamps. The resulting intensity was about three milliwatts per square centimeter at a temperature of about 103° Fahrenheit. Again, this heat was beyond the comfort zone. The forward current was reduced to about 5 milliamps. The resulting intensity was about two milliwatts per square centimeter at a temperature of about 93° Fahrenheit, which provided acceptable penetration and comfort level. This adjustment brought the temperature down to a comfortable level for the wearer.

For light delivery to the torso of an infant, the 30° LEDs 40 were found to be preferable because they covered a greater area with the same intensity and about the same temperature. In delivering light in other situations, the 15° LEDs 34 may be more suitable, because of the possibility of greater light penetration.

In another example shown in FIG. 4B, 15° LEDs 44 were used driven by a current of about 20 milliamps. The LEDs 44 each provided monochromatic light having a wavelength of about 470 nanometers and an intensity of about three milliwatts per square centimeter at a temperature of about 104° Fahrenheit. Again, this provided more heat than acceptable to be worn for any extended period. Accordingly, the forward current was reduced to about five milliamps. The resulting intensity was reduced to about two milliwatts per square centimeter at a temperature of about 93° Fahrenheit, which provided acceptable penetration and comfort level.

Another advantage of using an LED array is that a specific light frequency and wavelength can be selected that is advantageous for each application. In the present implementation for delivering light to the torso region of an infant, it was found that light having a wavelength of about 470 nanometers was effective in breaking down excessive bilirubin. All wavelengths mentioned above include a wavelength range of about plus or minus fifteen nanometers. That is, a peak wavelength of 470 nm is applied having a narrow wavelength range in a bell curve with a half peak bandwidth of 15 nanometers.

Referring now to FIG. 5, an implementation of the light pad apparatus of the present disclosure is shown in which the LED array is completely encapsulated in a waterproof material 52. This waterproof material may be of any suitable material, such as plastic, and is likely to be thick enough to not allow a puncture, yet clear enough to enable suitable transmission of light.

Figure 6A:
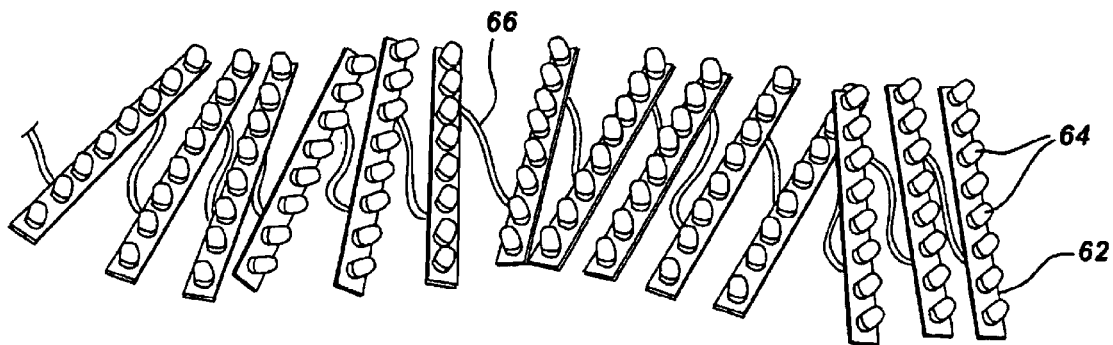
FIGS. 6A and 7 are schematic views showing substrate strips used in one implementation of the light pad.

Referring now to FIG. 6A, an implementation is shown for constructing the light pad 12 shown in FIG. 1. As shown in FIG. 6A, each of a plurality of light strips 62 has several LED units 64 spaced from each other in a row on each strip 62. The LED units 64 on each strip 62 are electrically coupled. Wires 66 connect the LED units 64 of each strip 62 to the LED units 64 of the adjoining strips. Strips 62 are preferably made of a rigid substrate material so as to allow high-intensity, through-hole LEDs and to maintain the LEDs in position. However, strips 62 are thin and spaced slightly apart from each other in a flexible pad, so that the pad can easily bend to conform to the surface of the body portion, such as to wrap around the body of an infant. Alternately, strips 62 may be a combination of rigid material around the LED units to enable precision attaching of the through-hole LEDs. The rest of each strip could be made of a flexible material, such as mylar or plastic.

Figure 6B:
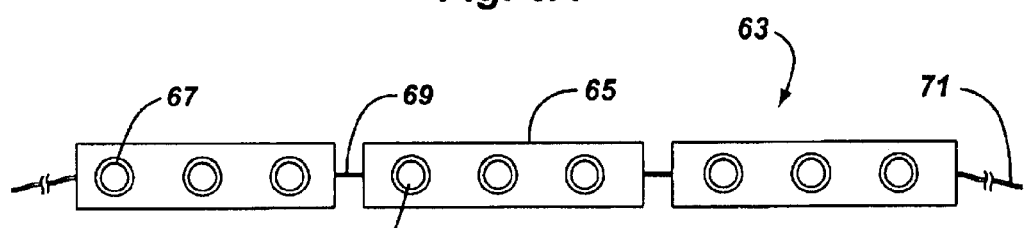
FIGS. 6B and 6C are schematic views showing alternative implementations of the substrate strips shown in FIGS. 6A and 7.
Figure 6C:
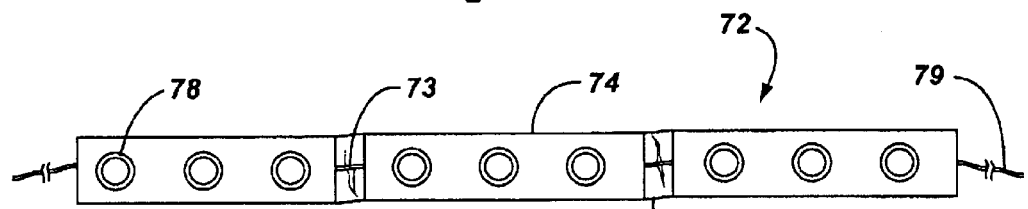

FIG. 6B shows an alternative implementation in which each strip 63 has three sets of smaller strips 65, each with three LEDs 67 therein. Wires 69 connect the LEDs together in each of the substrips 65. Wires 71 extend from both ends of strip 63 to connect the LEDs 67 to the LEDs 67 in adjacent strips (not shown). Another variation is shown in FIG. 6C, in which each of the strips 72 are formed of three substrips 74 connected together by flexible pieces 76, such as mylar. As in FIG. GB wires 73 connect the LEDs 78 in substrips 74. Additional wires 79 extend from either end of strip 72 to connect to the LEDs 78 in adjacent strips (not shown).

Figure 7:
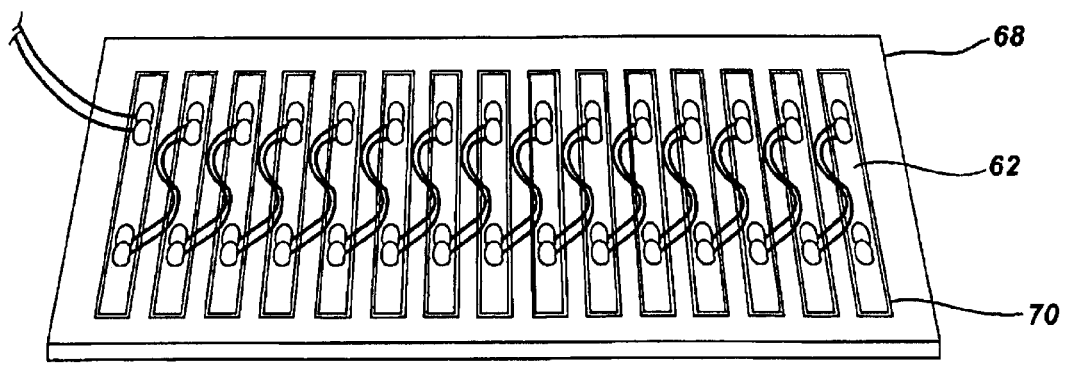

FIG. 7 shows the back side of a pad 68 with the strips 62 shown in FIG. 6A mounted therein. Preferably, spaced-apart cavities 70 are formed in the pad 68 and sized to accept the strips 62. The cavities include holes on the front side (not shown) for the LED units 64 to direct light out of the front of the pad, similar to the padding 12 around LED array 32 shown in FIG. 3A.

This pad construction provides strength and stable positioning of the LEDs using the strips 62. At the same time, the placement of the strips in a flexible pad 12 enables the device to be wrapped around an infant's body or other body part. Moreover, the alternate implementations shown in FIGS. 2B–2C are substantially increased in flexibility using pad 68 shown in FIG. 7.

Operation of the Apparatus

An example of the operation of the implementation of the present disclosure shown in FIGS. 2A–2D is as follows. The subject infant 24 may be positioned on the light pad 12 as shown in FIG. 2A and treated in that position. Alternately, for more effective coverage, the subject may have the pad 12 wrapped around the infant's body or torso, as shown in FIGS. 2B and 2C. The LEDs deliver light directly to the skin of the subject, as discussed earlier. As shown in FIG. 2D the power source 12, if it is a battery pack, and the controller 14 may be placed in a box 22 or other carrying container. The devices are light enough for a caretaker to carry in box 22 in one hand while carrying the infant, wrapped in pad 12 in the other hand.

Apparatus 10 is used by activating the controller 14 with power from the power source 16, which in turn enables the light pad 1246 to provide light to the subject as long as the system is operational. The controller insures that a suitable range of power is supplied to the LEDs, as discussed earlier.

In one instance, using an implementation of the disclosure described above, an array of nine by sixteen LEDs is provided, each powered at about five milliamps of current, with each LED having a voltage of about 3.3 volts. The array was operated at about 9.9 volts with 240 milliamps. The power source 16 was a battery pack, comprising a nine-volt rechargeable Ni-MH or NiCad battery. The subject was a newborn infant that was jaundiced with an excess of bilirubin. Light having a wavelength of 470 nm was emitted from LEDs at an angle of 30°. The light was applied to the infant as long as possible every day for 4–5 days. The result showed an improvement, characterized by a drop in biliruben count from an unacceptably high count of 18 or more to an acceptable count of 14 or less.

As a further implementation of the present disclosure, controller 14 may be programmed to process the corresponding LED light pads through duty cycles, in which the light pads are switched repeatedly on and off. Such duty cycles may have any combination of on and off times and may be set to operate at low frequencies or at higher frequencies of hundreds or thousands of cycles per second. This duty cycle operation enables the use of light of higher intensity than would ordinary be used without causing the buildup of heat that would be uncomfortable to the wearer. The use of more intense light enables deeper penetration of light to the body so that more effective treatment may be achieved in certain cases where greater light intensity is needed.

For instance, in the preceding examples, if a higher intensity of light is desired to achieve deeper penetration, one may apply the more intense light in a duty cycle with equal on and off times, so that the light is effectively applied to the body only half of the time that the light pad is turned on. In this application, since the light intensity has been substantially increased the use of a duty cycle lessens the total application of light so that there is no uncomfortable heat buildup. However, the reduction in the amount of light applied is compensated for by the increased intensity of light, enabling the desired treatment through deeper penetration.

Referring now to FIGS. 8A–8C, another implementation of the present disclosure is shown in the form of a vest 80. A front section 82 and a back section 83 are each comprised of a flexible material having multiple through-hole LEDs 84 similar to those shown in FIG. 1. LEDs 84 are disposed on the inside of the front section 82 and the back section 83 of vest 80 to direct light to the infant 81, as best seen in FIGS. 8A and 8B. Front and back sections 82, 83 are joined together by a center section 86 having an orifice 87 in the middle of section 86, for slipping over the head of an infant 81. Attachment straps 88 extend from each side of back section 83 to connect to attachment pieces 89 mounted on each side of front section 82. Combined controller/power source 85 is connected to vest 80 to deliver the necessary power and control.

One advantage to this vest implementation is that the separation of front and back sections 82, 83 provides for openings on each side of the infant 81, which enables some circulation of air inside the vest. This air circulation conducts away heat, thereby improving the comfort of the infant. This advantage is important where the vest 80 may be worn for most of several consecutive days. The vest 80 also tends to hold the unit in place and prevent slippage down the infant's torso.

Figure 9A:
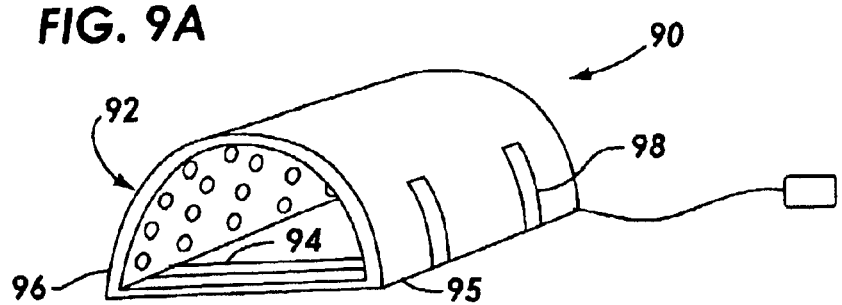
FIGS. 9A–9C are schematic views showing an alternative tent implementation.
Figure 9B:
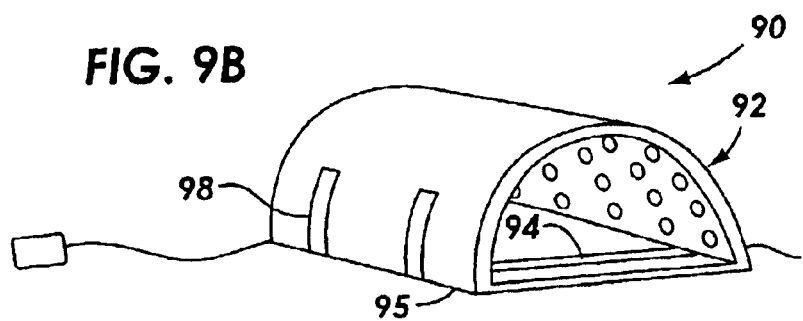
Figure 9C:
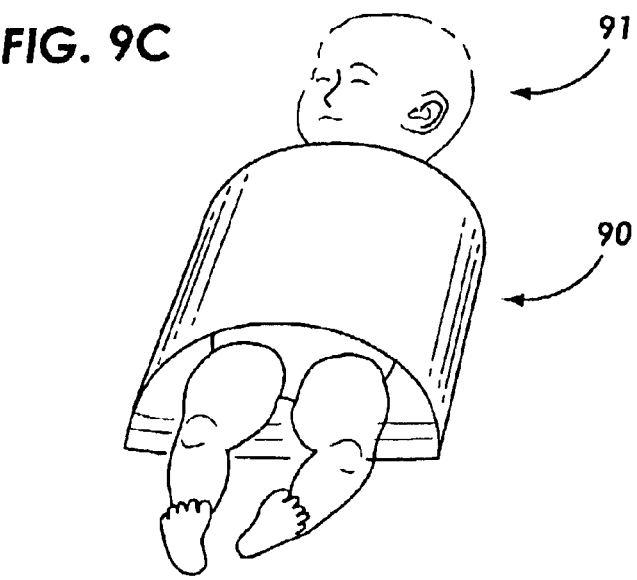

FIGS. 9A, 9B and 9C show another implementation of the present disclosure in the shape of a small arcuate tent 90. In this implementation, the pad 92 is shaped essentially the same as rectangular pad 12 in FIG. 1. Because the pad 92 is flexible, it can be bent in an arcuate shape as shown to fit over the infant's body without touching the skin. The pad 92 is held in place by elongated attachment straps 94 that extend from the front portion 95 to the back portion 96 of pad 92 and connect at attachment points 98.

In the tent implementation, there is even more space between an infant 91 and the tent-shaped blanket 90 than in the earlier described blanket and vest implementations. This enables even more cooling of the infant 91 by the free circulation of air. This arrangement is especially useful for maximum comfort while the infant 91 is sleeping, as heat is reduced by the air space between infant 91 and the tent-shaped blanket 90, and the child 91 may move freely within the tent 90. This implementation does not enable the infant 91 to be easily transported. However, when the infant 91 must be carried or otherwise transported, the tent 90 may be easily converted to a blanket as shown in FIGS. 2A–2D, by simply pulling the attachment members to draw the blanket around the infant.

Although the above implementations are representative of the present disclosure, other implementations will be apparent to those skilled in the art from a consideration of this specification and the appended claims, or from a practice of the implementations of the disclosed disclosure. It is intended that the specification and implementations therein be considered as exemplary only, with the present disclosure being defined by the claims and their equivalents.

What is claimed is:

1. A portable light-emitting device for delivering light to the blood supply of a human body of a subject through a non-ocular area of skin on the body, comprising:
   (a) a light delivery unit having a flexible pad with multiple spaced-apart apertures therein for positioning to conform to a portion of the body;
   (b) a plurality of through-hole LEDs, each extending at least partially through one of the apertures of the light delivery unit for emitting light outward from the light delivery unit toward the body;
   (c) a power supply connected to the light delivery unit for delivering power to the LEDs; and
   (d) a controller unit disposed between the power supply and the light delivery unit for controlling the delivery of power to the LEDs with sufficient intensity for the LEDs to deliver light to the blood supply.

2. The device of claim 1, wherein the through-hole LEDs are mounted on a plurality of rigid members, each flexibly connected to adjacent rigid members, and wherein the LEDS are each disposed in an aperture of the flexible pad one of the rigid members.

3. The device of claim 1, wherein the through-hole LEDs are mounted on a plurality of members, each member including at least one rigid portion supporting one of the through hole LEDS, and at least one flexible portion connecting at least one adjacent rigid portion.

4. The device of claim 1, wherein the LEDs are selected to provide light having wavelengths within a range of about 460–480 nanometers.

5. The device of claim 1, wherein the LEDs are selected to provide light within a range of light intensity of two to three milliwatts ver square centimeter.

6. The device of claim 1, wherein the LEDs are selected to provide light within an angle of light illumination in the range of about 15–30 degrees.

7. The device of claim 1, wherein the controller unit further comprises a control device to vary the power supplied to the light delivery unit.

8. The device of claim 7, wherein the control device is a high-speed switching device for switching power off and on in multiple duty cycles during the time that light is provided by the light delivery unit.

9. The device of claim 7, wherein the LEDs are disposed to deliver light to a portion of the body having a portion of the blood supply near a skin surface.

10. The device of claim 7, wherein the control device is a programmable device having a data input to automatically vary the power supplied to the light delivery unit, according to the data provided to the control device.

11. The device of claim 1, wherein the flexible pad has a structure adapted for disposing next to the skin of a patient.

12. The device of claim 11, wherein the flexible pad structure further comprises multiple independent strips of substrate, each substrate containing at least one light source, the strips being connected together to form the light delivery unit.

13. The device of claim 12, wherein the multiple independent strips of substrate are separately disposed in the flexible pad to enable the pad to be wrapped around a portion of the body of the subject.

14. The device of claim 11, wherein the flexible pad structure is sufficiently flexible to enable the pad to be wrapped around the patient's torso, and further comprising an attachment device for holding the pad around the torso.

15. The device of claim 11, wherein the flexible pad structure forms a flexible vest to be worn on the patient's torso, and further comprising an attachment device for holding the pad around the torso.

16. The device of claim 11, wherein the flexible pad structure is disposed to form an arcuate tent within which the patient may be placed, and further comprising an attachment device for holding the pad in the form of an arcuate tent.

17. A light-emitting device for delivering light to the blood supply of a human body of a subject through a non-ocular area of skin on the body, comprising:
(a) a flexible unit for positioning on a portion of the body having a plurality of spaced apart apertures therein;
(b) a plurality of through-hole light emitting diodes (LEDs), each LED being disposed on the flexible unit to extend at least partially through one of the apertures to direct light to the the blood supply of the body; and
(c) a power supply connected to the LEDs for delivering power thereto.

18. The device of claim 17 further comprising a substrate disposed on the flexible unit for supporting the LEDs.

19. The device of claim 18, wherein the substrate comprises a plurality of rigid strips of substrate each having at least one aperture therein for supporting an LED therein.

20. The device of claim 19, and further comprising a plurality of indentations on the flexible unit, each for supporting one of the rigid strips so that the LEDs are disposed to direct light through the apertures in the flexible unit.

21. The device of claim 17, and further comprising a controller between the power supply and the LEDs for controlling the power supplied to the LEDs.

22. The device of claim 21, wherein the controller includes a device for controlling the amount of voltage being supplied to the LEDs.

23. The device of claim 21, wherein the controller provides power to the LEDs in multiple duty cycles.

24. The device of claim 21, wherein the controller includes a device for shutting off the power to the LEDs in the event of an undesirable power disruption of the normal power supply to the LEDs.

25. A method using a portable light-emitting device to deliver light to the blood supply of a human body of a subject through a non-ocular area of skin on the body, comprising:
(a) positioning on a portion of the body a light delivery unit having a flexible pad with multiple spaced-apart apertures therein;
(b) directing light to the blood supply of a portion of the body from a plurality of individual through-hole LEDs, each being disposed at least partially within one of the apertures of the light delivery unit;
(c) providing power to the LEDs from a power supply connected to the light delivery unit; and
(d) controlling the delivery of power to the LEDs with a controller unit disposed between the power supply and the light delivery unit for controlling the delivery of power to the LEDs with sufficient intensity for the LEDs to deliver light to the blood supply.

26. The method of claim 25, wherein the LEDs each disposed to deliver light to a portion of the body having a portion of the blood supply near a skin surface.

27. The method of claim 25, wherein light is directed to a portion of the body having wavelengths within a range of about 460–480 nanometers.

28. The method of claim 25, wherein light is directed to a portion of the body within a range of light intensity of two to three milliwatts per square centimeter.

29. The method of claim 25, wherein light is directed to a portion of the body from each LED through one of the apertures, so as to provide light to the body within an angle of light illumination in the range of about 15–30 degrees.

30. The method of claim 25, wherein the power supplied to the light delivery unit is varied using a controller unit.

31. The method of claim 25, wherein the power supplied to the light delivery unit is varied using a high-speed switching device for switching power off and on in multiple duty cycles during the time that light is provided to the light delivery unit.

32. The method of claim 25, wherein the power supplied to the light delivery unit is varied using a programmable device to automatically vary the power supplied to the light delivery unit according to data provided to the programmable device.

33. The method of claim 25 wherein the light delivery unit is disposed around a portion of the body.

34. The method of claim 33, wherein the light delivery unit is wrapped around a portion of the body in the form of a blanket.

35. The method of claim 33, wherein the light deliver unit is disposed around the body in the form of a vest.

36. The method of claim 33, wherein the light delivery unit is disposed to be positioned above the body in the form of an arcuate tent.

37. A method of using a light-emitting device to deliver light to the blood supply of a human body of a subject through a non-ocular area of skin on the body, comprising:
(a) positioning a flexible unit having a plurality of spaced apart apertures therein on a portion of the body;
(b) disposing a plurality of through-hole light emitting diodes (LEDs) on the flexible unit, each LED being disposed on the flexible unit to extend at least partially through one of the apertures to direct light to the blood supply of the body; and
(c) providing power to the LEDs from a power supply connected to the LEDs for delivering power thereto with sufficient intensity to cause the LEDs to deliver light to the blood supply.

38. The method of claim 37, wherein the LEDs are disposed on a substrate comprising a plurality of rigid strips of substrate, each strip having at least one aperture therein for supporting an LED electrically connected to other LEDs on adjacent strips, and each strip being moveable independent of adjacent strips.

39. The method of claim 38, wherein the rigid strips of substrate are each disposed in an indentation on the flexible unit, so that the LEDs are positioned to direct light through the apertures in the flexible unit.

40. A portable light-emitting device for delivering light to the blood supply of a human body of a subject through a non-ocular area of skin on the body, comprising:
(a) a light delivery unit having multiple spaced-apart apertures therein for positioning on a portion of the body;

(b) a plurality of LEDs, each extending at least partially through one of the apertures of the light delivery unit for emitting light outward away from the light delivery unit;

(c) a power supply connected to the light delivery unit for delivering power to the LEDs;

(d) a controller unit disposed between the power supply and the light delivery unit for controlling the delivery of power to the LEDs; and (e) the controller unit having a high-speed switching device for switching power off and on in multiple duty cycles during the time that light is provided by the light delivery unit.

41. A portable light-emitting device for delivering light to the blood supply of a human body of a subject through a non-ocular area of skin on the body, comprising:

(a) a light delivery unit having multiple spaced-apart apertures therein for positioning on a portion of the body;

(b) a plurality of LEDs, each extending at least partially through one of the apertures of the light delivery unit for emitting light outward away from the light delivery unit;

(c) a power supply connected to the light delivery unit for delivering power to the LEDs;

(d) a controller unit disposed between the power supply and the light delivery unit for controlling the delivery of power to the LEDs; and (e) the light delivery unit further comprising a pad structure for disposing next to the skin of a patient, the pad structure being flexible to form an arcuate tent within which the patient may be placed, and further comprising an attachment device for holding the pad in the form of an arcuate tent.

42. A light-emitting device for delivering light to the blood supply of a human body of a subject through a non-ocular area of skin on the body, comprising:

(a) a flexible unit for positioning on a portion of the body having a plurality of spaced apart apertures therein;

(b) a plurality of light emitting diodes (LEDs), each LED being disposed on the flexible unit to extend at least partially through each of the apertures to direct light to the body;

(c) a power supply connected to the LEDs for delivering power thereto;

(d) a substrate disposed on the flexible unit for supporting the LEDs;

(e) wherein the substrate comprises a plurality of rigid strips of substrate each having at least one aperture therein for supporting an LED therein; and (f) a plurality of indentations on the flexible unit, each for supporting one of the rigid strips so that the LEDs are disposed to direct light through the apertures in the flexible unit.

43. A light-emitting device for delivering light to the blood supply of a human body of a subject through a non-ocular area of skin on the body, comprising:

(a) a flexible unit for positioning on a portion of the body having a plurality of spaced apart apertures therein;

(b) a plurality of light emitting diodes (LEDs), each LED being disposed on the flexible unit to extend at least partially through each of the apertures to direct light to the body;

(c) a power supply connected to the LEDs for delivering power thereto (d) substrate disposed on the flexible unit for supporting the LEDs; and (e) a controller between the power supply and the LEDs for controlling the power supplied to the LEDs, the controller including a device for shutting off the power to the LEDs in the event of an undesirable power disruption of the normal power supply to the LEDs.

44. A method using a portable light-emitting device to deliver light to the blood supply of a human body of a subject through a non-ocular area of skin on the body, comprising:

(a) positioning on a portion of the body a light delivery unit having multiple spaced-apart apertures therein;

(b) directing light to a portion of the body from a plurality of individual light sources, each being disposed at least partially within one of the apertures of the light delivery unit;

(c) providing power to the light sources from a power supply connected to the light delivery unit;

(d) controlling the delivery of power to the light sources with a controller unit disposed between the power supply and the light delivery unit; and (e) directing the light to a portion of the body from each LED through one of the apertures, so as to provide light to the body within a specifically-determined angle of light illumination body.

45. A method using a portable light-emitting device to deliver light to the blood supply of a human body of a subject through a non-ocular area of skin on the body, comprising:

(a) positioning on a portion of the body a light delivery unit having multiple spaced-apart apertures therein;

(b) directing light to a portion of the body from a plurality, of individual light sources, each being disposed at least partially within one of the apertures of the light delivery unit;

(c) providing power to the light sources from a power supply connected to the light delivery unit;

(d) controlling the delivery of power to the light sources with a controller unit disposed between the power supply and the light delivery unit; and (e) varying the power supplied to the light delivery unit using a high-speed switching device for switching power off and on in multiple duty cycles during the time that light is provided to the light delivery unit.

46. A method using a portable light-emitting device to deliver light to the blood supply of a human body of a subject through a non-ocular area of skin on the body, comprising:

(a) positioning a light delivery unit having multiple spaced-apart apertures therein about a portion of the body above the body in the form of an arcuate tent;

(b) directing light to a portion of the body from a plurality of individual light sources, each being disposed at least partially within one of the apertures of the light delivery unit;

(c) providing power to the light sources from a power supply connected to the light delivery unit; and (d) controlling the delivery of power to the light sources with a controller unit disposed between the power supply and the light delivery unit; and (e) wherein the light delivery unit is disposed to be positioned above the body in the form of an arcuate tent.

* * * * *

UNITED STATES PATENT AND TRADEMARK OFFICE
CERTIFICATE OF CORRECTION

PATENT NO. : 6,811,563 B2
DATED : November 2, 2004
INVENTOR(S) : Henry C. Savage Jr. et al.

It is certified that error appears in the above-identified patent and that said Letters Patent is hereby corrected as shown below:

<u>Column 10,</u>
Line 46, change "three milliwatts ver square centimeter" to -- three milliwatts per square centimeter --.

Signed and Sealed this

Seventeenth Day of May, 2005

JON W. DUDAS
*Director of the United States Patent and Trademark Office*